United States Patent [19]

Barton et al.

[11] 4,036,864

[45] July 19, 1977

[54] CHEMICAL PROCESS

[75] Inventors: Derek Harold Richard Barton, London, England; Robert Henry Hesse, Cambridge, Mass.

[73] Assignee: Research Institute for Medicine and Chemistry Inc., Cambridge, Mass.

[21] Appl. No.: 581,283

[22] Filed: May 27, 1975

[51] Int. Cl.$^2$ ................................................ C07J 1/00
[52] U.S. Cl. .................... 260/397.3; 260/239.55 R; 260/397.45
[58] Field of Search ........................................................
/Machine Searched Steroids; 260/397.3, 397.45

[56] References Cited

U.S. PATENT DOCUMENTS 3,687,943  8/1972  Barton et al. ............... 260/239.55 A

*Primary Examiner*—Elbert L. Roberts
*Attorney, Agent, or Firm*—Bacon & Thomas

[57] ABSTRACT

Saturated organic compounds containing a hydrogen atom bound to a tertiary carbon atom may be electrophilically fluorinated by reaction with an electrophilic fluorinating agent such as molecular fluorine or trifluoromethyl hypofluorite under conditions whereby the formation of free fluorine radicals is suppressed, e.g. by the presence of a free radical inhibitor such as oxygen or nitrobenzene, the reactants being substantially homogeneously dispersed in a liquid medium, e.g. a solvent medium such as fluorotrichloromethane or chloroform/fluorotrichloromethane, so that the said hydrogen atom is electrophilically replaced by a fluorine atom. The fluoroination is highly selective and, in the case of complex substrates such as saturated steroids which contain a number of tertiary C—H bonds, may be substantially completely confined to replacement of the hydrogen atom at the tertiary carbon atom which has the highest electron density about the C—H bond. The electron density and thus the direction of the fluorination may be controlled by appropriate selection of substituent groupings in the substrate molecule.

Novel 14α-fluorosteroids are also disclosed, including compounds having valuable androgenic or progestational activity and useful synthetic intermediates.

25 Claims, No Drawings

CHEMICAL PROCESS

This invention relates to a novel process for the introduction of fluorine into organic compounds and to novel fluorinated products which may be obtained thereby.

The introduction of fluorine into organic structures is known to give valuable results in many fields. Thus in the field of steroids, for example, introduction of fluorine, e.g. at the 9- or 6-positions, has been found to enhance physiological activity. In general the fact that fluorine and hydrogen are similar in size but very different in electronegativity means that replacement of hydrogen by fluorine in a biologically active compound will change or potentiate the activity of the compound.

In previously proposed methods for fluorination at saturated carbon atoms it has been thought necessary to employ free fluorine radicals. Consequently, even when reagents capable of electrophilic fluorination, for example molecular fluorine or trifluoromethyl hypofluorite, have been used, the system has been irradiated with ultraviolet or visible light, if necessary in the presence of an initiator such as benzoyl peroxide, to ensure the production of free radicals. Metal and metal salt catalysts have also been used in such fluorination reactions to initiate free radical formation. An inherent disadvantage of these fluorination reactions, by virtue of the free radical mechanism by which they proceed, is that the specificity and selectivity of the fluorination is generally low. Thus, for example, fluorination of a sensitive substrate such as a saturated steroid using free radical conditions tends to lead to the formation of a complex mixture of fluorinated products, so that isolation of a particular fluorinated product may require complicated separation techniques and normally affords only a comparatively low yield of the desired product.

We have found that organic compounds may in fact by fluorinated at saturated carbon atoms by an electrophilic mechanism on treatment with an electrophilic fluorinating agent if steps are taken to suppress competing free radical reactions. The electrophilic fluorination reaction is inherently more directional then free radical fluorinations, being strongly influenced by the electron densities about individual bonds in the fluorination substrate, as evidenced by, for example, the fact that the reaction is substantially completely confined to the fluorination of tertiary saturated carbon atoms. Thus fluorination of saturated organic substrates (as hereinafter defined) by this technique generally leads to a cleaner, more specific and more selective reaction than do the known free radical fluorination techniques.

According to one aspect of the present invention, therefore, we provide a process for the electrophilic fluorination of a saturated organic compound containing a hydrogen atom bound to a tertiary carbon atom which comprises reacting together the said compound and an electrophilic fluorinating agent substantially homogeneously dispersed in a liquid medium in the presence of a substance suppressing free radical reactions (hereinafter referred to as a "free radical inhibitor"), whereby formation of free fluorine radicals is suppressed and the said hydrogen atom is electrophilically replaced by a fluorine atom, and recovering the thus-obtained tertiary organic fluoride.

By the term "saturated organic compound" as used in this specification we mean a compound wherein all the carbon-carbon linkages are saturated or wherein any carbon-carbon multiple bonds are substantially completely deactivated against electrophilic fluorination under the reaction conditions employed, e.g. by substitution with one or more strongly electron-withdrawing groups; the compound may contain multiple bonds to atoms other than carbon, e.g. in substitutent groupings, provided that these multiple bonds do not react to a significant extent with the fluorinating agent. The term "tertiary carbon atom" designates a carbon atom which is bonded to three other carbon atoms and which is also bonded to a hydrogen atom.

The electrophilic fluorinating agent used in the process of the invention may, for example, be a hypofluorite wherein the fluoroxy group is bonded to an inert electron attracting group, which may be either inorganic or organic. Suitable inorganic hypofluorites include fluorosulphur hypofluorites such as pentafluorosulphur hypofluorite. Organic hypofluorites which may be used include lower (e.g. $C_{1-6}$) fluoroalkyl hypofluorites, the fluoroalkyl portions of which preferably contain at least two fluorine atoms per carbon atom. Examples of such organic hypofluorites include trifluoromethyl, perfluoropropyl, perfluoroisopropyl, perfluoro-t-butyl, monochlorohexafluoropropyl and perfluoro-t-pentyl hypofluorites and difluoroxy compounds such as 1,2-difluoroxytetrafluoroethane and difluoroxydifluoromethane. The use of trifluoromethyl hypofluorite is particularly preferred by virtue of its good selectivity and comparative ease of handling.

Molecular fluorine may also be employed as the electrophilic fluorinating agent in the process of the invention. Where fluorine is used in this way it is preferably either diluted with an inert gas such as nitrogen or argon, the concentration of fluorine in the resulting gas mixture conveniently being in the range 1-20% v/v, e.g. 3-16% v/v, or is introduced into the reaction system undiluted but at reduced pressure, e.g. less than 100 mm Hg, in order to moderate the reaction and facilitate control.

The fluorination is normally conducted in a liquid medium which is a solvent medium for the saturated organic compound to be fluorinated. The solvent need not be completely inert to the reaction conditions and in many cases will act as a free radical inhibitor as described in more detail hereinafter. Suitable solvents include lower alkanoic acids such as acetic acid; fluorinated lower alkanoic acids such as trifluoroacetic acid; fluorinated or fluorinated and chlorinated lower alkanes such as fluorotrichloromethane, chlorotrifluoromethane, dichlorodifluoromethane or 1,1,2-trichlorotrifluoroethane; fluorinated lower alkanols such as 2,2,2-trifluoroethanol; hydrates, e.g. the sesquihydrate, of hexafluoroacetone; nitriles such as acetonitrile; sulphones, e.g. di(lower alkyl)sulphones such as dimethylsulphone or cyclic sulphones such as sulpholane; and lower nitroalkanes such as nitromethane (the qualifiaction "lower" is used in this specification to designate molecules or groups containing up to 6 carbon atoms). Partially chlorinated lower alkanes such as chloroform or methylene chloride may also be employed as solvent, although such chloroalkanes have a tendency to react with the fluorinating reagent, which may therefore have to be used in excess to achieve optimum yields of the desired fluorinated product. Mixtures of solvents, e.g. fluorotrichloromethane and chloroform, may be used if desired. Cosolvents, e.g. water, lower alkanols such as methanol or ethanol, and cyclic ethers such as dioxan or tetrahydrofuran, may also be employed.

Some displacement of the newly introduced fluorine atoms by solvent molecules may occur when solvents such as alkanols and carboxylic acids, which contain nucleophilic centres, are used, although this tendency is reduced if steps are taken, e.g. as described hereinafter, to remove the hydrogen fluoride normally formed as a by product of the fluorination reaction.

We have found that the efficiency of the fluorination reaction is greatly impaired unless steps are taken to ensure that the reaction mixture remains essentially homogeneous throughout the course of the reaction. It will be appreciated that selection of a liquid medium which is a solvent for the saturated organic compound will assist in achieving even dispersion of the saturated organic compound in the reaction mixture. Fluorinating agents such as gaseous or volatile liquid hypofluorites or fluorine/inert gas mixtures are advantageously passed into the reaction mixture in gaseous form in such a way as to ensure good dispersion of the gas within the solution, for example by passage through a sintered dispersion tube or a perforated disc or foil. The reaction mixture is also desirably stirred or otherwise agitated to enhance dispersion of the fluorinating agent. Hypofluorite reagents are generally highly soluble in the commonly employed reaction media, so that adequate dispersion of these reagents can be effected comparatively easily. Elemental fluorine has a substantially lower solubility, however, so that efficient dispersion of the fluorine/inert gas mixture as it enters the reaction mixture and vigourous agitation of the mixture are required to produce the desired degree of homogeneity.

Alternatively the fluorinating agent may be employed in solution, e.g. in one of the solvents listed above, or in liquid form, e.g. in the case of a liquid hypofluorite having comparatively low volatility; mixing of this fluorinating agent solution with the reaction mixture containing the saturated organic compound is desirably accompanied by vigorous stirring or other agitation to enhance dispersion of the fluorinating agent.

Where the fluorination is conducted in a solvent medium the concentration of the reactants in the reaction solution is desirably kept comparatively low in order to ensure substantially homogeneous reaction conditions. Thus, for example, we prefer to employ comparatively dilute solutions of the saturated organic compound, e.g. solutions containing 4-500 millimoles per liter of said compound. Similarly, where a gaseous hyopfluorite reagent is employed it may be advantageous to admix this with an inert gaseous diluent such as nitrogen before its introduction into the reaction solution. The homogeneity of the reaction solution is further enhanced if the fluorinating agent is added slowly over a period of time, e.g. 2-24 hours, to the solution of the saturated organic compound.

The reaction temperature is preferably kept relatively low, the optimum temperature for a given reaction depending on, inter alia, the reactivity of the fluorinating agent, Hypofluorites, for example, may conveniently be employed at temperatures in the range $-78°$ to $+40°$ C; more reactive hypofluorites such as pentafluorosulphur hypofluoride may be used at lower temperatures within this range, whereas milder fluorinating agents such as trifluoromethyl hypofluorite may be employed at higher temperatures, e.g. in the range $-25°$ to $+25°$ C. Reactions involving molecular fluorine are generally conducted at somewhat lower temperatures, e.g. in the range $-100°$ to $0°$ C, conveniently at from $-80°$ to $-75°$ C.

As indicated above, the fluorination is conducted in the presence of a free radical inhibitor in order to suppress competing free radical reactions which would detract from the selectivity and specificity of the electrophilic fluorination reaction. We have found oxygen to be a very effective free radical inhibitor for this purpose. In some cases oxygen will already be present in sufficient quantity in the reaction system, for example as a contaminant of nitrogen used to dilute a gaseous fluorinating agent or in solution in the reaction solvent, to inhibit any radical reactions; alternatively, sufficent radical inhibition may be achieved if the reaction is conducted in the presence of air, for example using a partially open reaction vessel. In other instances it may be desirable actually to introduce oxygen or air into the reaction system to obtain satisfactory radical inhibition.

Other free radical inhibitors which may be employed include nitro-substituted aromatic hydrocarbons, for example nitrobenzene or m-dinitrobenzene, and quinones, for example benzoquinone.

The amount and nature of the free radical inhibitor used in a given fluorination reaction will to some extent depend on the particular electrophilic fluorinating agent employed. Thus, for example, hypofluorites such as trifluoromethyl hypofluorite are somewhat more prone to free radical formation than molecular fluorine and may require large quantities of inhibitor or the use of more potent inhibitors to suppress fully any radical reactions.

As indicated above, the reaction solvent may in certain cases act as a free radical inhibitor, as may any cosolvent used therewith. Thus, for example, solvents or cosolvents containing one or more reactive hydrogen atoms bound to carbon, for example partially chlorinated hydrocarbons such as chloroform or methylene chloride or cyclic ethers such as tetrahydrofuran, will suppress free radical reactions in cases wherein hypofluorites are employed as the fluorinating agent, although the degree of inhibition achieved in such solvents may be somewhat less than that obtained by the use of the above-described free radical inhibitors such as oxygen, nitrobenzene and benzoquinone. In cases where molecular fluorine is employed as the fluorinating agent, most solvents will have at least a partial inhibitory effect on any competing free radical reactions. This will generally be complemented by the inhibitory effect of traces of oxygen which will normally be present in the reaction system if it has not been purposely excluded, so that in many cases solution reactions using, for example, a fluorine/nitrogen gas mixture as the fluorinating agent may not in fact require the addition of a separate free radical inhibitor.

A side reaction which may accompany the fluorination process of the invention comprises elimination of the newly-introduced fluorine atom together with a hydrogen atom from an adjacent carbon atom, with consequent formation of a carbon-carbon double bond. The double bond may subsequently react with the fluorinating agent leading to the formation of a range of fluorinated by-products, which may be unwanted. The elimination is catalysed by hydrogen fluoride, which is in most cases a by-product of the fluorination process; the elimination is also effectively autocatalytic since it is necessarily accompanied by the formation of hydrogen fluoride.

We have found that this side reaction may be suppressed to a substantial degree if the fluorination process is carried out in the presence of a substance which will bind or absorb hydrogen fluoride, for example a weak base (e.g. an alkali metal salt of an organic acid, for example a lower alkanoic acid such as acetic acid or a halogenated, preferably fluorinated, lower alkanoic acid such as trifluoroacetic acid, or an anhydrous alkali metal fluoride such as sodium or potassium fluoride), a dried and activated molecular sieve or an organosilicon compound which contains a bond to silicon that is easily cleaved by hydrogen fluoride to give a silyl fluoride and which is unreactive to the fluorinating agent (e.g. a siloxane such as hexamethyldisiloxane, a silyl ether such as methyl trimethylsilyl ether, a silyl ester such as trimethylsilyl acetate or a silylamide such as N,O-bis(-trimethylsilyl) trifluoroacetamide). We prefer to use weak bases such as sodium trifluoroacetate or sodium or potassium fluoride as a basic hydrogen fluoride binding agent when a hypofluorite is employed as the fluorinating agent since stronger bases such as sodium or potassium acetate tend to promote decomposition of the hypofluorite, although such stronger bases are tolerated when, for example, elemental fluorine is employed as fluorinating agent.

Crude reaction products obtained by the fluorination process of the invention may also be prone to decompose by elimination of hydrogen fluoride in a similar manner to that described above, particularly when a hypofluorite fluorinating agent has been employed, the autocatalytic decomposition being initiated by hydrogen fluoride formed from the breakdown of impurities such as carbonyl difluoride. It may therefore be advantageous, especially where no base has been added previously, to add a base, for example a tertiary organic base such as pyridine or triethylamine, to the crude reaction product to bind any hydrogen fluoride which is liberated and so stabilise the desired fluorinated product; such treatment is particularly desirable when there is to be any delay in the isolation and purification of the desired product.

Saturated organic compounds which may be fluorinated in accordance with the process of the invention include compounds of formula

(I)

wherein either (A) R¹, R² and R³ (which may be the same or different) are each selected from alkyl groups containing up to 30 carbon atoms, preferably 1-20 carbon atoms, e.g. methyl, ethyl, propyl, butyl, octyl, decyl, stearyl and eicosyl; saturated mono- and polycyclic (including bicyclic) cycloaliphatic groups containing up to 30 carbon atoms, more preferably 5-25 carbon atoms, and optionally containing one or more heteroatoms selected from O,N and S, e.g. monocyclic cycloalkyl groups such as cyclopentyl or cyclohexyl, polycyclic (including bridged) cycloalkyl groups such as adamantyl or norbornyl, fused polycyclic structures such as saturated steroidal groups, sugar groups, and tetrahydrofuranyl and tetrahydrothienyl groups; and any of these groups substituted by one or more halogen atoms (i.e. fluorine, chlorine, bromine and iodine atoms), and/or oxo, cyano, nitro, hydroxy, protected (e.g. esterified) hydroxy (e.g. lower alkanoyloxy such as acetoxy, halogenated lower alkanoyloxy such as trichloroacetoxy or trifluoroacetoxy, nitrooxy, or nitro-substituted benzoyloxy such as p-nitrobenzoyloxy or 2,4-dinitrobenzoyloxy), lower alkoxy (e.g. methoxy or ethoxy), mercapto, sulphino, lower alkylthio (e.g. methylthio), lower alkylsulphinyl (e.g. methylsulphinyl), lower alkylsulphonyl (e.g. methylsulphonyl), acyl (e.g. lower alkanoyl such as acetyl), acylamino (e.g. trifluoroacetamido, N,N-diacylamino (e.g. phthalimido, succinimido or N,N-diacetylamino) or di(lower alkyl) amino (e.g. dimethylamino) groups; or (B) R¹ has any of the above-defined meanings and R² and R³ together with the attached carbon atom form an unsubstituted or substituted saturated mono- or polycyclic cycloaliphatic group as defined in (A) above; or (C) R¹, R² and R³ togehter with the attached carbon atom form an unsubstituted or substituted polycyclic cycloaliphatic group as defined in (A) above.

As indicted above, the organic substrate may contain carbon-carbon multiple bonds provided that these are substantially completely deactivated against electrophilic fluorination under the reaction conditions employed, e.g. by substitution with one or more strongly electron-withdrawing groups; in general multiple bonds present in aromatic groups are more susceptible to such deactivation than are aliphatic multiple bonds. Thus the compounds of formula I may contain aromatic groups (e.g. phenyl) substituted by one or more strongly electron-withdrawing groups such as nitro, sulphonyl (e.g. lower alkylsulphonyl such as methylsulphonyl), esterified sulphonyl (e.g. lower alkoxysulphonyl such as methoxysulphonyl) or amido, or by a divalent electron-withdrawing group such as an amidodicarbonyl group (e.g. so that the substituted aromatic groups forms a phthalimido group). Such aromatic groups may not be totally inert to the fluorination reaction, but will in general react substantially more slowly than saturated tertiary carbon atoms. The aromatic groups may for example be present as or in protecing groups used to substitute and deactivate reactive groups such as amino or hydroxy present in any of R¹, R² and R³, as described in greater detail hereinafter. Since such protecting groups are normally removed at a later stage of the reaction sequence, partial fluorination of the aromatic group in such circumstances will not affect the nature of the final product.

Reactive groups such as primary or secondary amino which may be present in fluorination substrates as substituents or in nitrogen-containing heterocyclic systems should be protected prior to fluorination, for example by acylation to yield an amide derivative or by reaction with a strong acid such as fluoroboric, sulphuric or hexafluorophosphoric acid to yield a salt. Simple carboximides and sulphonamides will tend to undergo N-fluorination under the conditions employed for the electrophilic fluorination, so that protecting amide groups should be formed from strongly deactivating (i.e. electron withdrawing) acyl moieties such as trifluoroacetyl, or the amino groups (if primary) should be protected as an N,N-diacylamino groups (e.g. an N,N-phthaloyl-, N,N-succinoyl- or N,N-diacetyl-amino group), if such N-fluorination is undesired.

Mercapto and sulphide groups present in fluorination substrates are susceptible to attack by the fluorinating agent, leading ultimately to formation of a sulphide or sulphoxide group. Where it is desired to avoid such side reactions any mercapto or sulphide groups present in the substrate may effectively be protected by oxidation to sulphoxide or, more preferably, sulphone groups prior to the fluorination.

It may also be advantageous to protect any hydroxy substituents, e.g. by esterification, prior to fluorination. The use of esters derived from perfluoro lower alkanoic acids such as trifuoroacetic acid may be of value in this respect since such esterification will increase the polar effect of the hydroxyl group and may thus influence the direction of the fluorination reaction as described hereinafter. Ester groups derived from perfluorinated acids such as trifluoroacetic acid may also readily be removed after the fluorination by hydrolytic or hydrogenolytic cleavage. Other useful protecting ester groups include inorganic groups such as nitro and ester groups derived from lower aliphatic acids (e.g. lower alkanoic and halogenated lower alkanoic acids such as acetic or trichloroacetic acid) and aromatic acids wherein the aromatic ring carries one or more strongly electron-withdrawing substituents (e.g. p-nitrobenzoic acid or 2,4-dinitrobenzoic acid).

Where it is desired to fluorinate a saturated carbon atom in a substrate containing a carbon-carbon double bond the double bond may effectively be "protected" by halogenation of the substrate to yield an α,β-dihalo derivative, e.g. by treatment with molecular bromine in a solvent such as acetic acid, by treatment with dioxan dibromide in a solvent such as ether or carbon tetrachloride: chloroform, or by treatment with molecular chlorine in a solvent such as benzene. A preferred bromination technique comprises reaction with excess dioxan dibromide in carbon tetrachoride: chloroform (ca 2:1) in the dark in the presence of potassium carbonate. The double bond may subsequently be regenerated by dehalogenation of the compound, e.g. by treatment with zinc and acetic acid or ammonium acetate.

As indicated above, the electrophilic nature of the fluorination process of the invention causes the direction, and similarly the rate, of the fluorination to be influenced strongly by the electron density about individual bonds in the reaction substrate. One consequence of this is that fluorination in accordance with the invention effectively occurs only at tertiary carbon atoms. This behavior may be contrasted with that observed in free radical fluorination reactions wherein, for example, secondary carbon atoms are fluorinated at not unduly dissimilar rates to tertiary carbon atoms (tertiary carbon atoms typically reacting at 2–4 times the rate for secondary carbon atoms). The process of the invention is therefore of particular value in the selective fluorination of tertiary carbon atoms in saturated organic substrates.

It will be appreciated that some of the possible groups listed above for $R^1$, $R^2$ and $R^3$ contain a CH grouping capable of being fluorinated by the electrophilic mechanism of the process of the invention. It is an advantage of the process, however, that the fluorinating agent will attack predominantly the site having the highest electron density, and such sites can normally be identified in the substrate on a conventional theoretical basis. A substrate having more than one CH group may, of course, be represented in terms of $R^1R^2R^3CH$ in different ways; in general the preferred representation should be that in which the CH group shown possesses a higher electron density than any other CH group present.

It will similarly be appreciated that where, for example, a substrate contains two tertiary carbon atoms which have similar electron densities about the respective C—H bonds, fluorination may occur at either of these tertiary carbon atoms to give a mixture of two monofluorinated products. In general the incidence of difluorinated products is negligible in such circumstances, since the introduction of a fluorine atom at one tertiary carbon atom will in many instrances deactivate the other tertiary carbon atom or atoms as regards further electrophilic fluorination.

An example of the selective fluorination of a tertiary carbon atom using the process of the invention is afforded by the fluorination of adamantane by treatment with, for example, trifluoromethyl hypofluorite in the presence of air. The adamantane is fluorinated cleanly and exclusively at the tertiary 1-position, no significant fluorination taking place at the secondary 2-position under the conditions required for reaction at the 1-position. Introduction of the electronegative fluoro substituent at the 1-position effectively deactivates the remaining tertiary carbon atoms in the molecule so that no electrophilic reaction is observed at these carbon atoms unless more vigorous conditions are employed.

It will be apparent from the above that the presence of polar substituents in the saturated organic substrate will significantly affect the course of the electrophilic fluorination by virtue of their influence on the electron density in the substrate molecule. Thus, for example, the rate of the fluorination reaction will generally be decreased by the presence of an electron withdrawing group in the vicinity of the tertiary carbon reaction center. This may be illustrated by the fluorination, e.g. using trifluoromethyl hypofluorite in the presence of air, of 1-trifluoroacetamidoadamantane, which reacts at about half the rate of adamantane itself, to give the tertiary 3-fluoro derivative. 1-Trifluroacetoxyadamantane is flourinated even more slowly under such conditions, so that a mixture of adamantane and 1-trifluoroacetoxyadamantane may be treated with, for example, a fluorine/nitrogen gas mixture containing a small proportion of oxygen to promote selective fluorination of the unsubstituted adamantane component only.

This deactivating effect of electron withdrawing substituents may be employed to advantage in directing the fluorination in cases where complex substances containing several non-equivalent tertiary carbon atoms are required to be fluorinated at a single carbon atom, for example in the preparation of monofluorinated steroid derivatives.

Thus a saturated steroid such as 5α-androstane

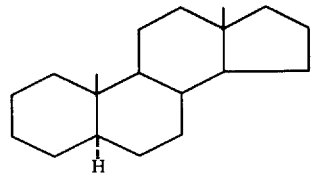

(II)

has in principle four tertiary carbon atoms, at the 5-, 8-, 9- and 14-positions respectively, which might be expected to undergo ready electrophilic fluorination in accordance with the process of the invention, although the 8-position carbon atom is in fact somewhat unreactive to such fluorination by virtue of the attached hydrogen atom being on the β-face of the molecule and thus being screened by the $C_{18}$ and $C_{19}$ methyl groups. It is possible, however, to direct the fluorination substantially exclusively to any of the other tertiary centers by use of appropriately substituted steroid starting materials.

Thus, for example, electrophilic fluorination of a saturated steroid in which there are electron-withdrawing substituents present on the A- and D- rings, for example a compound of formula

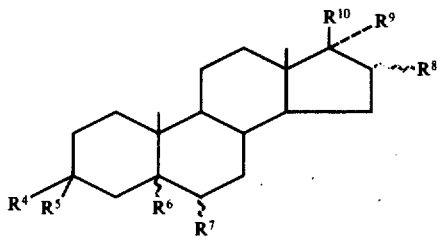

(III)

[where $R^4$ represents protected (e.g. esterified, etherified or silylated) hydroxy ($\alpha$- or $\beta$-) and $R^5$ represents hydrogen or $R^4$ and $R^5$ together represent a keto or protected keto (e.g. ketal) group, and $R^6$ and $R^7$ each represent hydrogen, or $R^4$ and $R^6$ together represent a 3,5-cyclo linkage, $R^5$ represents hydrogen and $R^7$ represents protected hydroxy ($\alpha$- or $\beta$-); $R^8$ represents hydrogen, methyl or protected hydroxy ($\alpha$- or $\beta$-); $R^9$ represents hydrogen, hydroxy or protected hydroxy and $R^{10}$ represents acetyl or substituted acetyl (e.g. hydroxyacetyl or, more preferably, protected hydroxyacetyl, e.g. esterified hydroxyacetyl such as acetoxyacetyl), or $R^9$ represents hydrogen and $R^{10}$ represents protected (e.g. esterified) hydroxy, or $R^9$ and $R^{10}$ together represent a keto group] such as $3\beta$, $17\beta$-di(trifluoroacetoxy)-5$\alpha$-androstane, leads to formation of the corresponding 9$\alpha$-fluoro derivative, e.g. having the formula

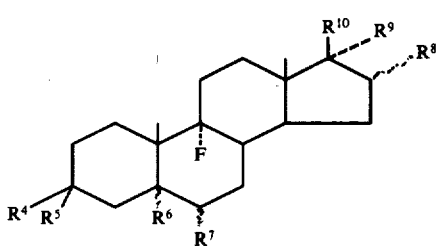

(IV)

(where $R^4$, $R^5$, $R^6$, $R^7$, $R^8$, $R^9$ and $R^{10}$ are as defined above), the 5- and 14-positions being deactivated to electrophilic attack by the proximity of the electron withdrawing substituents on the A- and D-rings, e.g. at the 3- and 17-positions respectively, and the 8-position being sterically hindered.

It may also be possible to obtain a proportion of the 14$\alpha$-fluoro analogue of a compound (IV) in the reaction product, especially if a starting material (III) in which $R^9$ and $R^{10}$ have comparatively low electron-withdrawing properties (e.g. a compound wherein $R^9$ is hydrogen or hydroxy and $R^{10}$ is acetyl or substituted acetyl such as acetoxyacetyl, or $R^9$ or $R^{10}$ together represent a keto group) is selected.

When a starting material (III) in which $R^7$ is a protected hydroxy group is employed and a 9$\alpha$-fluoro product is desired, the group $R^7$ is preferably one which is comparatively low electron-withdrawing properties (e.g. a lower alkanoyloxy group such as acetoxy) and so does not effect undue deactivation of the 9$\alpha$-position with regard to electrophilic reaction.

The electrophilic fluorination of a saturated steroid may similarly be directed substantially exclusively to the 14$\alpha$-position by selection of a starting material in which the A- and B-rings are substituted by electron-withdrawing atoms or groups. Thus, for example, electrophilic fluorination of a compound of formula

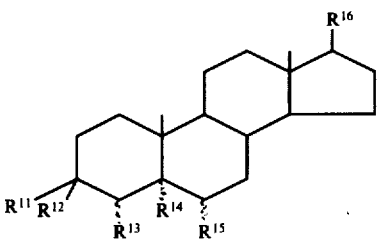

(V)

[where $R^{11}$ represents protected hydroxy ($\alpha$- or $\beta$-) and $R^{12}$ represents hydrogen or $R^{11}$ and $R^{12}$ together represent a keto or protected keto group, $R^{13}$ represents hydrogen and $R^{14}$ and $R^{15}$ both represent halogen (e.g. chloro or bromo), or $R^{14}$ together with $R^{13}$ or $R^{15}$ represents an epoxy group, the remaining $R^{13}$ or $R^{15}$ representing hydrogen, or $R^{11}$ $R^{14}$ together represent a 3,5-cyclo linkage, $R^{12}$ and $R^{13}$ each represent hydrogen, and $R^{15}$ represents protected hydroxy (e.g. esterified hydroxy such as acetoxy); and $R^{16}$ represents oxo, acetyl or protected hydroxy (e.g. esterified hydroxy such as acetoxy)] such as 5$\alpha$, 6$\beta$-dibromo-3$\beta$-trifluoroacetoxyandrostan-17-one or 5$\alpha$, 6$\beta$-dibromo-3$\beta$-trifluoroacetoxypregnan-20-one, leads to formation of the corresponding 14$\alpha$-fluoro derivative having the formula

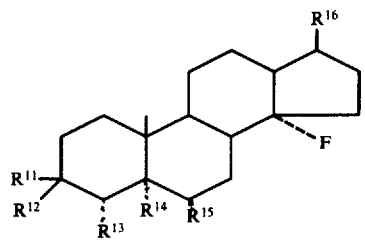

(VI)

(wherein $R^{11}$, $R^{12}$, $R^{13}$, $R^{14}$, $R^{15}$ and $R^{16}$ are as defined above), the 9-position being deactivated by the electronegative substituents present at the 5- and/or 6-positions.

It may also be possible to obtain a proportion of the 9$\alpha$-fluoro analogue of a compound (VI) in the reaction product, especially if a starting material (V) in which $R^{14}$ and $R^{15}$ have comparatively low electron-withdrawing properties (e.g. a compound in which $R^{11}$ and $R^{14}$ form a 3,5-cyclo linkage, $R^{12}$ and $R^{13}$ represent hydrogen, and $R^{15}$ is acetoxy) is selected.

Steroids having a 17$\beta$-hydrocarbon group possess a nuclear tertiary hydrogen atom at the 17$\alpha$-position, but this position is less susceptible to fluorination than the 9- or 14-positions. When, however, there are electron withdrawing substituents on the B-ring, and preferably also the A-ring, the 9- and 14- positions are deactivated and the 17$\alpha$-position is fluorinated (unless there is a nearby electron withdrawing group, such as a 20-keto group). Thus electrophilic fluorination in accordance with the invention of a compound of formula -continued

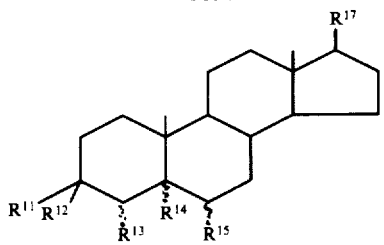

(VII)

(where $R^{11}$, $R^{12}$, $R^{13}$, $R^{14}$ and $R^{15}$ are as defined above and $R^{17}$ is a saturated hydrocarbon group e.g. containing 2-12 carbon atoms, for example the —CH(CH$_3$).(CH$_2$)$_3$.CH(CH$_3$)$_2$ side chain characteristic of cholesterol) such as 5α,6β-dichloro-3β-trifluoroacetoxycholestane, leads to formation of the corresponding 17α-fluoro derivative, e.g. having the formula

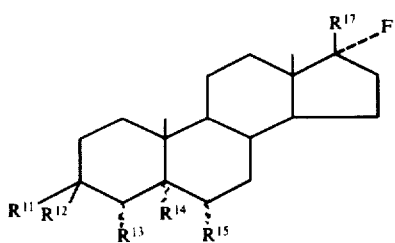

(VIII)

(where $R^{11}$, $R^{12}$, $R^{13}$, $R^{14}$, $R^{15}$ and $R^{17}$ are as defined above), in view of the deactivation of the 9- and 14-positions. The tertiary hydrogen atoms in the side chain are less active, as is usual, than any of the tertiary hydrogen atoms in the ring-structure.

Where any of $R^4$, $R^7$, $R^8$, $R^9$, $R^{10}$, $R^{11}$, $R^{15}$ and $R^{16}$ in formulae (II)-(VIII) represent or contain protected hydroxy groups these protected hydroxy groups may, for example, be esterified hydroxy groups as described above (e.g. lower alkanoyloxy such as acetoxy, halogenated lower alkanoyloxy such as trichloroacetoxy or trifluoroacetoxy, nitroaroyloxy such as p-nitrobenzoyloxy or 2,4-dinitrobenzoyloxy, and inorganic ester groups such as nitrooxy); etherified hydroxy groups such as lower alkoxy (e.g. methoxy, ethoxy, n-propoxy, isopropoxy or t-butoxy), aralkoxy (e.g. phenyl lower alkoxy such as benzyloxy, diphenylmethoxy or triphenylmethoxy) or aryloxy (e.g. phenoxy); or silyloxy groups such as lower alkyl-, aralkyl- (e.g. phenyl lower alkyl-) or aryl-(e.g. phenyl-) substituted silyloxy [e.g. tri(lower alkyl) silyloxy such as trimethylsilyloxy]. Such protecting groups may be introduced by, for example, conventional methods; thus hydroxy groups may be silylated by reaction of the hydroxy compound with an appropriate halosilane or silazane, e.g. a tri(-lower alkyl) silyl halide or hexa (lower alkyl) disilazane.

Where $R^4$ and $R^5$ in formulae III and IV or $R^{11}$ and $R^{12}$ in formulae V-VIII together represent a ketal group they may, for example, each be lower alkoxy such as methoxy or ethoxy or may together represent a lower alkylenedioxy group such as ethylenedioxy.

The above described behaviour of steroid substrates in the process of the invention, which may readily be predicted on a conventional theorectical basis, is in total contrast to that observed in the free radical fluorination of such steroids, when all the tertiary centres are attached equally and indiscriminately.

A further advantage of the process of the invention in the fluorination of complex substrates such as steroids is that the reaction proceeds with retention of configuration. While we do not wish to be bound by theoretical considerations it would appear that the fluorination proceeds by an $S_E2$ mechanism involving formation of pentacoordinate carbonium ions by insertion of F$^+$ into the tertiary C—H bond, since other reactions of this type are known to lead to retention of configuration.

It will be appreciated from the above that the process of the invention possesses wide-ranging applications in the fluorination of saturated organic compounds containing tertiary carbon atoms. Thus, for example, the process may be used to prepare fluorinated adamantane derivatives which are valuable intermediates in the synthesis of compounds possessing antiviral and/or spasmolytic activity and which may thus be used in, for example, combatting influenza viruses and treating Parkinson's disease. Fluorinated adamantane derivatives and other tertiary fluorinated saturated aliphatic hydrocarbons which may be prepared in accordance with the invention have also been shown to act as effective Friedel Crafts alkylating agents in the presence of catalysts such as antimony pentafluoride or phosphorus pentafluoride.

The process of the invention is of particular value in the fluorination of steroids, especially since the configuration of the steroid is unaffected by the electrophilic fluorination reaction.

It is well known that introduction of a 9-fluorine atom into a biologically active steroids in many cases significantly enhances the activity of the compound; the electrophilic fluorination process of the invention provides a convenient route to a range of active fluorosteroids of this type. Thus, for example, 3β,17β-di(trifluoroacetoxy)-5α-androstane may readily be converted to its 9α-fluoro anologue, which latter compound may subsequently be converted by known methods to, for example, androgenically active 9α-fluorosteroids such as 9α-fluoro-11β,17β-dihydroxy-17α-methylandrost-4-en-3-one (Halotestin).

Introduction of a 9α-fluoro atom into an appropriately substituted corticosteroid, followed by dehydrofluorination to form a $\Delta^{9,11}$-double bond provides a convenient route to corticosteroids substituted at the 9- and/or 11-positions and obviates the need to use, for example, ring C-oxygenated precursor starting materials such as hecogenin or to employ a microbiological hydroxylation reaction to functionalise the 11-position. 9,11-Dehydro steroids of use as intermediates in the synthesis of 9- and/or 11-substituted anabolic steroids may similarly be prepared using this approach.

Alternatively, steroids carrying electron withdrawing substituents on the A- or B-rings, for example the above-described compounds of formula V, may be fluorinated in accordance with the invention to yield the corresponding 14-fluorosteroid, which will exhibit physiological activity of the same general type as the parent unfluorinated steroid, but usually at a modified level of activity. Such fluorosteroids, for example the compounds of formulae VI, may readily be converted to the 14-fluoro analogues of known biologically active, particularly androgenic and progestational, steroids.

Thus, for example, 5α,6β-dibromo-14α-fluoro-3β-trifluoroacetoxyandrostan-17-one may be converted to 14α-fluorotestosterone by a process involving debromination to yield the corresponding Δ⁵,⁶compound, reduction to yield 3β,17β-dihydroxy-14α-fluoroandrost-5(6)-ene, and selective oxidation at the 3-position (e.g. by Oppenauer oxidation following benzoylation of the 17-hydroxy group) to yield the 3-oxo-Δ⁴-steroid. Similarly, deprotection of the 3-trifloroacetoxy group in the Δ⁵,⁶ compound and oxidation of the resulting hydroxy group (e.g. using Jones reagent) affords 14α-fluoroandrost-4-ene-3,17-dione; this last compound possesses valuable anabolic activity, exhibiting an enhanced level of oral activity compared to its 14α-hydrogen analogue.

5α,6β-Dibromo-14α-fluoro-3β-trifluoroacetoxypregnan-20-one may be converted to 14α-fluoroprogesterone by debromination and reduction or hydrolysis to yield the corresponding 3-hydroxy-Δ⁵,⁶-steroid, and oxidation to the desired 3-oxo-Δ⁴-steroid; 14α-fluoroprogesterone exhibits a higher level of progestational activity on oral administration than does its 14α-hydrogen analogue. A range of 14α-fluorocorticosteroids may be prepared by similar methods.

Similarly, appropriately substituted steroids having a hydrocarbon group at the 17β-position may be converted in accordance with the invention to their 17α-fluoro analogues. Thus, for example, 5α,6β-dichloro-3β-trifluoroacetoxycholestane may be fluorinated at the 17α-position and the resulting 17α-fluorosteroid may be converted to 17α-fluorocholesterol by dechlorination and hydrolytic or hydrogenolytic cleavage of the trifluoroacetyl group at the 3-position.

14-Fluorosteroids, for example the 14-fluoro derivatives described above, are novel compounds, possessing useful biological activity as hereinbefore described or constituting intermediates for active compounds, and comprise a further feature of the present invention.

Novel 14α-fluorosteroids embraced by the invention include compounds having the formula

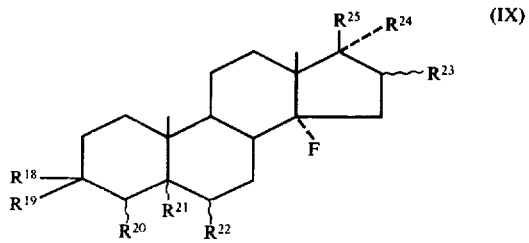

(IX)

where R¹⁸ represents hydroxy or protected hydroxy (e.g. esterified hydroxy such as acetoxy, trifluoroacetoxy or nitrooxy) and R¹⁹ represents hydrogen (α- or β-), or R¹⁸ and R¹⁹ together represent a keto or protected keto (e.g. ketal) group, R²⁰ represents hydrogen and R²¹ and R²² both represent hydrogen or halogen (e.g. chlorine or bromine) or together form a double bond or an epoxy group, and when R¹⁸ and R¹⁹ together represent a keto group, R²⁰ and R²¹ may together form a caron-carbon double bond or an epoxy group, R²² then being hydrogen, or R¹⁸ and R²¹ together form a 3,5-cyclo linkage, R¹⁹ and R²⁰ then being hydrogen and R²² being hydroxy or protected hydroxy (e.g. esterified hydroxy such as acetoxy); R²³ represents hydrogen, methyl, hydroxy or protected hydroxy (α-or β-); R²⁴ represents hydrogen, hydroxy or protected hydroxy (e.g. esterified hydroxy such as acetoxy) and R²⁵ represents acetyl or substituted acetyl (e.g. hydroxyacetyl or protected hydroxyacetyl, for example acyloxyacetyl such as acetoxyacetyl), or R²⁴ represents hydrogen and R²⁵ represents hydroxy or protected hydroxy (e.g. esterified hydroxy such as acetoxy) or R²⁴ and R²⁵ together represent a keto group.

Fluorinated steroids obtained in accordance with the invention may also be of value in the synthesis of various unsaturated steroids, since it is possible to promote elimination of the fluorine atom together with a hydrogen atom from an adjacent carbon atom so that a carbon-carbon double bond is formed. The elimination may be promoted by acid catalysis, suitable catalysts including hydrogen fluoride and Lewis acids such as boron trifluoride, conveniently employed in the form of an etherate. Dehydrofluorination of, for example, 14-fluorosteroids obtained in accordance with the invention provides a convenient route to a range of Δ¹⁴-steroids of value as intermediates in the synthesis of medically important cardenolides.

The following Examples serve to illustrate the invention. All temperatures are in ° C. Where bottles of fluorine are referred to, these contain an overall gas pressure of about 3 atmospheres.

EXAMPLE 1

Fluorination of Adamantane using Trifluoromethyl Hypofluorite i. A solution of adamantane (250 mg, 1.84 mmole) in fluorotrichloromethane (30 ml) at −25° was treated with gaseous trifluoromethyl hypofluorite (2 mmoles), air being admitted to the reaction vessel during the course of the gas addition.

After 30 minutes the reaction product was isolated by evaporation of the solvent in vacuo and was shown by g.l.c. to contain 69% of 1-fluoroadamantane, 4% of polyfluorinated adamantane derivatives and 27% of unreacted adamantane. The FMR spectrum of the product showed a single peak at φ* + 128 (s) ppm.

A repeat of the above procedure in which degassed fluorotrichloromethane was employed as the solvent and air was excluded from the reaction system gave a product containing (as measured by g.l.c.) 46% of 1-difluoroadamantane, 24% of polyfluorinated adamantane derivatives and 30% of unreacted adamantane. The FMR spectrum of this product showed peaks at φ* + 49 (s), 128 (s), 130 (s), 130 (s), 174 (m) and 182 (m) ppm, confirming that the absence of a free radical inhibitor such as oxygen led to the formation of a range of fluorinated by-products.

ii. A solution of adamantane (250 mg, 1.84 mmole) in degassed fluorotrichloromethane (30 ml) to which had been added benzoquinone (195 mg, 1.84 mmole) was treated at −25° with trifluoromethyl hypofluorite (2 mmoles).

After 30 minutes the fluorotrichloromethane was evaporated off in vacuo, the residue was added to hexane, and the resulting solution was filtered to remove benzoquinone and derivatives thereof. The reaction product was shown by g.l.c. to contain 71% of 1-fluoroadamantane, 6.5% of polyfluorinated adamantanes and 22.5% of unreacted adamantane.

EXAMPLE 2

Fluorination of Adamantane using Molecular Fluorine

A solution of adamantane (272 mg, 2 mmole) in a mixture of fluorotrichloromethane (200 ml) and ethanol-free chloroform (20 ml) was treated at −75° with a slow stream of fluorine (6% v/v in nitrogen, total quantity of fluorine ca. 5 mmole) over a period of 4 hours, the fluorine/nitrogen gas mixture being introduced with vigorous stirring into the reaction solution through a sintered glass disc. The solution was subsequently flushed well with nitrogen, washed successively with aqueous sodium bicarbonate and water and was then dried.

The reaction product was obtained by evaporation of the solvent in vacuo and was shown by g.l.c. (3% Hi-efficiency 6 foot coloumn, temperature 135°, nitrogen flow rate 15 ml/min.) to consist of 75% 1-fluoroadamantane, 9% more polar material (principally polyfluorinated derivatives) and 16% unreacted adamantane.

The product was chromatographed on silica gel (75 g). Elution with hexane gave adamantane (40 mg) identical with an authentic sample (IR spectroscopy and g.l.c. retention time); elution with chloroform : hexane (1:9) gave 1-fluoroadamantane (232 mg) which was recrystallized from hexane. This recrystallised product (219 mg, 83.5% based on recovered starting material) had m.p. 261°-263° (sealed tube), a single FMR peak at $\phi^*$ + 128.5 (s) ppm, and IR spectrum identical with an authentic sample.

EXAMPLE 3

Fluorination of 1-Trifluoroacetamidoadamantane using Trifluoromethyl Hypofluorite A solution of 1-trifluoroacetamidoadamantane (3 g, 12.1 mmole) in fluorotrichloromethane (40 ml), containing nitrobenzene (1.5 g, 12.2 mmole), was treated with trifluoromethyl hypofluorite (13 mmole) at −25° for 17 hours, air being admitted to the reaction vessel during this time. The solution was then purged with nitrogen to remove excess trifluoromethyl hypofluorite and the solvent was removed in vacuo. The residue was dissolved in chloroform, washed with aqueous sodium bicarbonate and water, and then dried, whereafter the product was chromatographed on silica gel (100 g). Elution with chloroform initially afforded unreacted starting material (70 mg), followed by 3-fluoro-1-trifluoroacetamido adamantane (2.1 g), which appeared homogeneous by g.l.c. After recrystallisation from ether:hexane this product exhibited m.p. 66.5°-68.5°.

EXAMPLE 4

Fluorination of 1-Trifluoroacetoxyadamantane using Trifluoromethyl Hypofluorite

A solution of 1-trifluoroacetoxyadamantane (1.0 g, 4.0 mmole, prepared by reacting adamantan-1-ol with trifluoroacetic anhydride in dry pyridine) in fluorotrichloromethane (10 ml), containing m-dinitrobenzene (80 mg, 0.48 mmole), was treated with trifluoromethyl hypofluorite (4.5 mmole) at −25° for 24 hours, air being admitted to the reaction vessel during this time. The product was recovered in a similar manner to that described in Example 3 and was chromatographed on silica (100 g). Elution with chloroform:hexane (1:5) afforded unreacted starting material (152 mg), while elution with chloroform:hexane (1:4) gave liquid 3-fluoro-1-trifluoroacetoxyadamantane (489 mg) which appeared homogeneous by g.l.c. This product sublimed at 70° (bath)/1 mm Hg to give a crystalline solid m.p. 28°-32°; $\nu_{max}$ (film) 1780 cm$^{-1}$; PMR 1.5-2.6 (m, adamantyl protons); FMR $\phi^*$ + 76.2 (s, CF$_3$COO—) and + 133.5 (broad s) ppm.

Fluorination of 1-trifluoroacetoxyadamantane in chloroform at room temperature, using trifluoromethyl hypofluorite in the absence of air and free radical inhibitors such as m-nitrobenzene, gave a complex mixture of products showing a large number of peaks on g.l.c. analysis. The FMR spectrum of this product indicated the presence of several monofluoro derivatives and a mixture of polyfluorinated derivatives, indicating that the fluorination has proceeded principally by a free radical mechansim.

EXAMPLE 5

Fluorination of Adamantan-1-ol using Trifluoromethyl Hypofluorite

A solution of adamantan-1-ol (0.75 g, 5 mmole) in 2,2,2-trifluoroethanol (10 ml), containing nitrobenzene (70 mg, 0.57 mmole), was treated with trifluoromethyl hypofluorite (5.5 mmole) at −25° for 8 hours, whereafter the reaction solution was purged with nitrogen and the product recovered in a similar manner to that described in Example 3. Recrystallisation from ether:hexane gave a mixture of 3-fluoroadamantan-1-ol and 3,5-difluoroadamantan-1-ol (ca. 6:1 by g.l.c. analysis and integration of FMR peaks $\phi^*$+ 133 (s) and + 139 (s) ppm) (0.52 g, ca 60%). The 3-fluoroadamantan-1-ol component was isolated by p.l.c. (silica gel, eluting with chloroform:hexane) and was verified by microanalysis and by comparison (IR, PMR, FMR) with 3-fluoroadamtan-1-ol obtained by hydrolysis (using methanolic sodium hydroxide at room temperature) of 3-fluoro-1-trifluoroacetoxyadamantane prepared as in Example 4.

EXAMPLE 6 i. Fluorination of 3β, 17β-Di (trifluoroacetoxy)-5α-androstane using Trifluoromethyl Hypofluorite A well-stirred solution of 3β, 17β-di(trifluoroacetoxy)-5α-androstane (2.5 g, 5.15 mmole, prepared by treatment of 5α-androstane-3β,17β-diol with trifluoroacetic anhydride in pyridine), nitrobenzene (800 mg, 6.5 mmole) and sodium trifluoroacetate (10 g, 73.5 mmole) in fluorotrichloromethane (45 ml) was treated with trifluoromethyl hypofluorite (8.5 mmole) at −20° for 2.5 hours, air being admitted to the reaction vessel during this time. Thereafter the solution was purged with nitrogen and the solvent was removed in vacuo. The residue was dissolved in chloroform and the resulting solution was washed with aqueous sodium bicarbonate and water and was then dried, whereafter the product was chromatographed on silica gel (125 g). Elution with chloroform:hexane (3:7) gave unreacted starting material (308 mg), while subsequent elution with chloroform:hexane (7:13) gave 3β,17β-di(trifluoroacetoxy)-9α-fluoro-5α-androstane (1.02 g), which crystallised from hexane as prisms (917 mg) m.p. 140°-142°; $[\alpha]_D^{24}$ −22° (c 1.47, CHCl$_3$). (Found C,55.10; H,5.78; F,26.35%;m/e 502. C$_{33}$H$_{29}$O$_4$F$_7$ requires C,54.97; H,5.82; F,26.47%; M$^+$ 502).

ii. 9α-Fluoro-5α-androstane-3,17-dione

The product of (i) above (260 mg) in a mixture of methanol (25 ml), tetrahydrofuran (12 ml) and 2N aqueous sodium hydroxide (10 ml) was stirred at room temperature for 1 hour. Most of the solvent was evaporated off in vacuo and the residue was diluted with water, whereafter 3β,17β-dihydroxy-9α-fluoro-5α-androstane hydrate (210 mg) was recovered by filtration. The product crystallised from chloroform:hexane as prisms (179 mg) m.p. 195°-196°; $[\alpha]_D^{24}$ −10° (c 0.49, CHCl$_3$); $\nu_{max}$ 3550, 3400 and 3250 cm$^{-1}$; PMR spectrum includes signals at δ 0.75 (3H,s, 18-Me), 0.94 (3H,s, 19-Me) and 3.65 (2H, m, CH.OH); FMR φ* + 179.5 ppm (multiplet ca 80 Hz in width).

A sample of the 3,17-diol prepared as above (280 mg) in acetone (120 ml) at 0° was treated with an excess of Jones reagent (0.4 ml), using the method of Djerassi et al; J. Org. Chem. 21, 1547 (1956), for 15 minutes. Excess Jones reagent was destroyed by the addition of isopropanol (0.5 ml) and water (15 ml) was added. The organic solvents were then evaporated off in vacuo and the aqueous residue was treated with ether to give the title compound (268 mg), which crystallised from acetone:hexane as prisms (265 mg) m.p. 188°–189°; $[α]_D^{24}$ +82° (c 1.71, CHCl$_3$); $ν_{max}$ 1740 and 1725 cm$^{-1}$; PMR spectrum includes signals at δ0.89 (3H,s, 18-Me) and 1.15 (3H,s, 19-Me); FMR φ * +179.25 ppm (multiplet ca 80 Hz in width). (Found: C74.37; H,8.83; F,6.24. C$_{19}$H$_{27}$O$_2$F requires C,74.47; H,8.83; F,6.20%).

EXAMPLE 7

Fluorination of 3β,17β-Di(trifluoroacetoxy)-5α-androstane using Molecular fluorine A solution of 3β,17β-di(trifluoroacetoxy)-5α-androstane (968 mg, 2 mmole) in fluorotrichloromethane (300 ml) and chloroform (15 ml) was treated at −75° with a slow stream of fluorine (6% v/v in nitrogen, total quantity of fluorine ca 6.5 mmole) over a period of 3 hours, the fluorine:nitrogen gas mixture being introduced with vigorous stirring through a sintered glass disc. Thereafter the solution was purged with nitrogen and worked up in a similar manner to that described in Example 6(i), the recovered product being chromatographed on silica gel (125 g). Elution with chloroform:hexane (1:2) afforded a semi-crystalline solid (248 mg) comprising unreacted starting material together with 3β,17β-di(trifluoroacetoxy)-5α-androst-9(11)-ene. Further elution with chloroform-hexane (2:3) gave 3β,17β-di(trifluoroacetoxy)-9α-fluoro-5α-androstane, which was shown by g.l.c. to be 95% pure. The product crystallised from hexane as prisms (347 mg) m.p. 140°–142° and was found to identical (IR, PMR and g.l.c. retention time) to the product of Example 6(i).

EXAMPLE 8 i. Fluorination of 5α,6β-Dibromo-3β-trifluoroacetoxy-androstan-17-one using Trifluoromethyl Hypofluorite A solution of 5α, 6β-dibromo-3β-trifluoroacetoxy androstan-17-one (550 mg, 1 mmole, prepared from Δ$^{5,6}$-dehydroisoandrosterone by trifluoroacetylation using trifluoracetic anhydride in pyridine and bromination using dioxan dibromide in chloroform: carbon tetrachloride), nitrobenzene (360 mg, 2.9 mmole) and sodium trifluoroacetate (3.5 g, 25.7 mmole) in fluorotrichloromethane (45 ml) was treated with trifluoromethyl hypofluorite (3 mmole) for 6 hours at 0° and for a further 9 hours at room temperature. The solution was then purged with nitrogen and worked up in a similar manner to that described in Example 6(i) to yield a gum comprising crude 5α,6β-dibromo-14α-fluoro-3β-trifluoroacetoxy androstan-17-one (545 mg), the PMR spectrum of which included signals at δ 1.05 (3H, s, 18-Me) and 1.58 (3H, s, 19-Me).

The crude product, in ether (40 ml) and ethanol (40 ml), was treated with zinc dust (400 mg) and ammonium acetate for 17 hours at room temperature, whereafter the solution was filtered and the solvents removed in vacuo. The product was dissolved in ether and chromatographed by p.l.c. (silica gel). Elution with ethyl acetate: hexane (1 : 1) (×2) and recovery of the major band gave 14α-fluoro-3β-hydroxyandrost-5(6)-en-17-one (165 mg), which crystallised from acetone:hexane as prisms (144 mg) m.p. 160°–161°; $[α]_D^{24}$ + 2.5° (c 0.75, CHCl$_3$); $ν_{max}$ 3540 and 1745cm$^{-1}$; the PMR spectrum included signals at δ1.02 (6H, s, 18-Me and 19-Me), 3.5 (1H,m,3-CH.OH) and 5.42 (1H,m,6-CH); FMR φ * + 163.5 ppm (multiplet ca 80Hz wide). (Found: C, 74.27; H, 9.01; F, 6.04%; m/e 306. C$_{19}$H$_{27}$O$_2$F requires C, 74.47; H, 8.88; F, 6.20%; M+306).

ii. 14α-Fluoro-5α-androstane-3,17-dione

14α-Fluoro-3β-hydroxyandrost-5(6)-en-17-one (400mg) in ethanol (70 ml) was hydrogenated over palladium-charcoal (5%; 250 mg) until uptake of hydrogen ceased (72 hr). The solvent was evaporated in vacuo and the crude product was recrystallised from acetone:hexane to give prisms of 14α-fluoro-3β-hydroxy-5α-androstan-17-one (158 mg) m.p. 201°–202°; $[α]_D^{23}$ + 83° (c 0.84, CHCl$_3$); $ν_{max}$ 3500 and 1730 cm$^{-1}$; the PMR spectrum included signals at δ 0.83 (3H, s, 19-Me), 1.00 (3H, s, 18-Me) and 3.6 (1H, m, 3-CHOH); FMR φ * + 164 ppm (broad multiplet ca 80 Hz wide).

The hydrogenated product (122 mg) in acetone (30 ml) at 0° was treated with an excess of Jones reagent (0.15 ml) for 15 min., whereafter isopropanol was added and the product recovered in a similar manner to that described in Example 6 (ii). Recrystallisation from acetone:hexane afforded needles of the title compound (106 mg) m.p. 181°–182°; $[α]_D^{23}$ + 105.5° (c 0.63, CHCl$_3$); $ν_{max}$ 1725 and 1755 cm$^{-1}$; the PMR spectrum included a signal at δ 1.03 (6H, s, 18-Me); FMR φ * + 163.8 ppm (broad multiplet ca 80 Hz wide).

iii. 3β-Hydroxyandrost-5(6), 14-dien-17-one

A solution of 14α-fluoro-3β-hydroxyandrost-5(6)-en-17-one (200 mg), prepared as described in (i) above, in pyridine (20 ml) was treated with trifluoracetic anhydride (140 mg) at 0° for 10 minutes to give 14α-fluoro-3β-trifluoroacetoxyandrost-5(6)-en-17-one which was isolated and recrystallised from acetone:hexane as prisms (209 mg) m.p. 175°–176°; $[α]_D^{25}$ − 12.5° (c 4.1, CHCl$_3$).

This trifluoracetate (200 mg) in dry benzene (50 ml) was treated with boron trifluoride-etherate (150 mg) at room temperature for 10 min. Water (25 ml) was added, and the organic layer was separated and washed with sodium bicarbonate and water, and was then dried. Removal of the solvent in vacuo gave a gum which was chromatographed on Keisel gel GF 254 (150 g) eluting with ethyl acetate: hexane (1:9). The early fractions, which were shown by t.l.c. [ethyl acetate: hexane (1:9)] to contain a single spot (Rf 0.65), were combined to give 3-trifluoroacetoxyandrost-5(6), 14-dien-17-one (38 mg), which crystallised from acetone: hexane as prisms (32 mg) m.p. 160°–162°; $[α]_D^{24}$ + 46° (c 0.75, CHCl$_3$). Further elution of the column gave fractions shown by t.l.c. to contain a single spot (Rf 0.5); these were combined to give 3-trifluoroacetoxyandrost-5(6), 8(9)-dien-17-one (52 mg), the thermodynamic product of the elimination. This product crystallised from methanol (at −20°) as plates (15 mg) m.p. 109°–115°.

3-Trifluoroacetoxyandrost-5(6),14-dien-17-one (15 mg) in tetrahydrofuran (3 ml) and methanol (2 ml) was treated with 2N aqueous sodium hydroxide (1 ml) at 0° for 3 min. The solution was diluted with water (15 ml), the organic solvents were evaporated off in vacuo, and the residue was extracted with ether to give the title compound (11 mg), which crystallized from acetone-hexane as prisms (8 mg), m.p. 161°-164°, identical [IR and t.l.c. (ethyl acetate-hexane 1:3)] with an authentic sample. Two recrystallizations raised the m.p. to 165°-168°.

iv. 14α-Fluoroandrost-4-ene-3, 17-dione

A solution of 14α-fluoro-3β-hydroxyandrost-5(6)-en-17-one (93 mg), prepared as described in (i) above, in acetone (20 ml) was treated with Jones reagent (0.10 ml) at 0°-5° for 5 min. Excess Jones reagent was destroyed by the addition of isopropanol (0.2 ml) and water (5 ml) was added. The organic solvents were then evaporated off in vacuo and the aqueous residue was extracted with chloroform. The chloroform was evaporated in vacuo and the thus-obtained residue dissolved in warm methanol (10 ml). The resulting solution was treated with one drop of 2N aqueous sodium hydroxide and warmed on a steam bath for 5 min. The orange solution so obtained was neutralized with acetic acid, water was added, and the organic solvents were evaporated of in vacuo. The residue was extracted with chloroform, and the solution was washed with sodium bicarbonate and water, and then dried. Evaporation of the chloroform in vacuo gave a solid (92 mg) which was chromatographed by p.l.c. (silica gel) eluting with ethyl acetate:hexane (1:1). Recovery of the major band gave the title compound (68 mg), which crystallised from acetone as prisms (58 mg) m.p. 216°-217°; $[\alpha]_D^{24}$ + 181° (c 0.69, CHCl$_3$); $\lambda$max (ethanol) 239 nm ($\epsilon$ 12,900); $\nu_{max}$ 1740, 1660 and 1615 cm$^{-1}$; the PMR spectrum included signals at $\delta$1.05 (3H, s, 18-Me), 1.22 (3H, s,19-Me) and 5.8 (1H, s, 4-H); FMR $\phi^*$ + 164.5 ppm (broad multiplet ca 90 Hz wide). (Found: c, 74.82; H, 8.23; F, 6.30, C$_{19}$H$_{25}$O$_2$F requires C,74.97; H,8.28; F,6.24%).

EXAMPLE 9 i. Fluorination at 5α,6β-Dibromo-3β-trifluoroacetoxypregnan-20-one using Trifluoromethyl Hypofluorite a. Preparation of starting material Pregnenolone (10 g, 31.5 mmole) in pyridine (100 ml) was treated with trifluoracetic anhydride (7.5 g) at room temperature for 15 minutes to give 3β-trifluoracetoxy pregn-5(6)-en-20-one, which was isolated as an ethyl acetate solution and recrystallised from acetone as prisms (10.36 g) m.p. 155°-156°; $[\alpha]_D^{25}$ + 4.5° (c 1.63, CHCl$_3$).

The thus-obtained trifluoracetate (4.125g, 10 mmole) in chloroform (20 ml) and carbon tetrachloride (40 ml) was treated with dioxan dibromide (5g, 20 mmole) and the solution was stirred with potassium carbonate (10 g) at room temperature in the dark, for 16 hours. Excess bromine was removed in vacuo, and the solution was filtered, washed with water and dried. Evaporation of the solvent afforded 5α,6β-dibromo-3β-trifluoroacetoxypregnan-20-one, which was recrystallised from ether: hexane (yield 4.02 g) m.p. 142°-145°; $[\alpha]_D^{23}$ −15.5° (c 0.98, CHCl$_3$).

b. Fluorination

The 5α,6β-dibromo compound prepared in (a) above (1.145 g, 2 mmole), nitrobenzene (375 mg, 3 mmole) and sodium trifluoroacetate (4g, 29.5 mmole) were dissolved in fluorotrichloromethane (125 ml) and treated with trifluoromethyl hypofluorite (3 mmole) at −15° to −20° for 7 hours, air being admitted to the reaction vessel during this time. The solution was then purged with nitrogen and worked up in a similar manner to that described in Example 6 (i) to yield a gum comprising crude 5α,6β-dibromo-14α-fluoro-3β-trifluroacetoxypregnan-20-one, which was immediately treated with zinc dust (800 mg) and ammonium acetate (1.6g) in ether (80 ml) and ethanol (80 ml) for 24 hours at room temperature, whereafter the solution was filtered and the solvents removed in vacuo. The product was dissolved in ether and immediately chromatographed on a Kieselgel GF 254 column (150 g) eluting with ethyl acetate: hexane (2 : 3). Early fractions afforded pregnenolone (166 mg) while later fractions gave 14α-fluoropregnenolone (291 mg), which crystallised from acetone : hexane as prisms (256 mg) m.p. 198°-202° (dec); $[\alpha]_D^{23}$ + 32.5° (c 0.65, CHCl$_3$); max 3600 and 1695 cm$^{-1}$; the PMR spectrum included signals at $\delta$ 0.77 (3H, s, 18-Me), 1.00 (3H, s, 19-Me), 2.12 (3H, s, 21-Me), 3.0 (m, 17-H), 3.5 (m, 3-H) and 5.4 (1H, m, 6-H); FMR $\phi^*$ + 164 ppm (broad multiplet ca 90–100 Hz wide). (Found: C, 75:52; H, 9.25%; m/e 334. C$_{21}$H$_{31}$O$_2$F requires C, 75.41; H 9.34; F, 5.68%; M+ 334).

ii. 14;60-Fluoropregn-4-ene-3,20-dione(14α-Fluoroprogesterone)

The product of (i)(b) above (80 mg) in acetone (75 ml) at 0° was treated with Jones reagent (0.10 ml) for 5 min. The solution was then worked up as described in Example 8 (iv) and the thus-obtained crystalline product was chromatographed by p.l.c. (silica gel) eluting with ethyl acetate:hexane(2:3). Recovery of the major band gave the title compound (61 mg) which crystallized from acetone-hexane as prisms (57 mg) m.p. 175°-175.5°; $[\alpha]_D^{23}$ +204° (c 1.0, CHCl$_3$); $\nu_{max}$ 1695, 1665 and 1620 cm$^{-1}$; $\lambda_{max}$. (ethanol) 239 nm ($\epsilon$, 12,000); the PMR spectrum included signals at $\delta$0.73 (3H, s, 18-Me), 1.17 (3H, s, 19-Me), 2.11 (3H, s, 21-Me) and 5.8 (s, 4-H); FMR $\phi^*$ 164 ppm.

EXAMPLE 10

Fluorination of 5α,6β-Dichloro-3α-trifluoroacetoxycholestane using Trifluoromethyl Hypofluorite 5α,6β-DIchloro-3β-trifluoroacetoxycholestane dissolved in fluorotrichloromethane was reacted with trifluoromethyl hypofluorite in the presence of nitrobenzene and sodium trifluoroacetate in analogous manner to the process of Example 9 (i) (b). The product was treated with zinc dust and ammonium acetate in ether and ethanol and worked up us described in Example 9 (i) (b) to yield, after chromatography, 17α-fluorocholesterol m.p. 149°. (Found C, 80.23; H, 11.51; F, 4.15%. C$_{27}$H$_{45}$OF requires C, 80.20; H, 11.14; F 4.70%).

EXAMPLE 11

Fluorination of 3β-Acetoxy-17α-hydroxy-16βmethyl-5α-pregnan-20-one using Molecular Fluorine 3β-Acetoxy-17α-hydroxy-16β-methyl-5α-pregnan-20-one (1g, prepared by treatment of the corresponding 3β-ol with acetic anhydride in pyridine) was dissolved in fluorotrichloromethane (250 ml) and chloroform (200 ml) containing sodium trifluoroacetate (ca. 2g) and sodium fluoride (ca. 2g). The resulting solution was cooled to $-78°$ and vigourously stirred, whereupon fluorine from four 750 cc bottles (8–10% v/v fluorine in nitrogen) was added over 9–10 hours. The reaction solution was then poured into aqueous sodium thiosulphate and the organic layer was separated, washed with water, dried over potassium carbonate and evaporated to dryness. The residue was purified by liquid chromatography, eluting with cyclohexane containing 30% v/v ethyl acetate and 0.1% v/v pyridine, to yield $3\beta$-acetoxy-$9\alpha$-fluoro-$17\alpha$-hydroxy-$16\beta$-methyl-$5\alpha$-pregnan-20-one (50%); m.p. 150° (after recrystallisation from acetone); PMR spectrum includes signals at $\delta$ 2.20 (21-Me), 2.00 (3–0.CO.$\underline{CH}_3$), 0.92 (19-Me) and 0.87 (18-Me); FMR $\phi^*$ + 179.5 ppm. (Found: C, 70.51; H, 9.20; F, 4.48; $C_{24}H_{37}FO_4$ requires C, 70.55; H, 9.13; F, 4.65%).

Example 12

Fluorination of 21-Acetoxy-$17\alpha$-hydroxy-$16\beta$-methyl-$5\alpha$-pregnane-3,20-dione using Molecular Fluorine 21-Acetoxy-$17\alpha$-hydroxy-$16\beta$-methyl-$5\alpha$-pregnane-3,20-dione (1.3g, prepared by oxidation of the corresponding $3\beta$-ol with aqueous sodium dichromate/sulphuric acid/acetic acid) was dissolved in fluorotrichloromethane (250 ml) and chloroform (200 ml) containing sodium trifluoroacetate (ca. 2g) and sodium fluoride (ca. 2g). The resulting solution was cooled to $-78°$ and vigorously stirred, whereupon fluorine from four 750 cc bottles (9–10% v/v flourine in nitrogen) was slowly bubbled through the solution. The reaction solution was then poured into aqueous sodium thiosulphate and the organic layer was separated, washed with water, dried over potassium carbonate and evaporated to dryness. The residue was purified by liquid chromatography, eluting with methylene chloride containing 15% v/v ethyl acetate and 0.1% v/v pyridine, and two fractions were collected. The less polar fraction was 21-acetoxy-$14\alpha$-fluoro-$17\alpha$-hydroxy-$16\beta$-methyl -$5\alpha$-pregnane-3,20-dione (20%); m.p. 125° (after recrystallisation from acetone); PMR spectrum includes signals at $\delta$ 4.91 (2H, —$\underline{CH}_2$OAc), 2.17 (21 — O. CO.$\underline{CH}_3$), 1.03 (19-Me) and 0.90 (18-Me); FMR $\phi^*$ + 160 ppm (J "/2 + 80 Hz). (Found: C, 65.56; H, 8.71; F, 3.93; $C_{24}H_{35}FO_5$ requires C, 65.43; H, 8.47; F, 4.31%). The more polar fraction was 21-acetoxy-$9\alpha$-fluoro-$17\alpha$-hydroxy-$16\beta$-methyl-$5\alpha$-pregnane-3,20-dione (31%); m.p. 163° (after recrystallisation from acetone); PMR spectrum includes signals at $\delta$ 4.97 (2H, -$\underline{CH}_2$OAc), 2.18 (21-O. CO.$\underline{CH}_3$), 1.12 (19-Me) and 0.83 (18-Me); FMR $\phi^*$ + 179 ppm (J "/2 = ca. 80 Hz). (Found: C, 66.88; H, 8.79; F, 4.21; $C_{24}H_{35}FO_5$. ½ $H_2O$ requires C, 66.80; H, 8.47; F, 4.40%).

EXAMPLE 13 i. Fluorination of $3\beta$-Acetoxy-$5\alpha,6\beta$-dichloropregnan-20-one using Molecular Fluorine a. Preparation of starting material A solution of pregnenolone acetate (10g) in dry benzene was added in portions to a stirred solution of chlorine in benzene (60ml) and pyridine (0.5ml) until the yellow colour of the chlorine solution disappeared. Further chlorine was then added, followed by further portions of ths steroid solution until the yellow colour again disappeared. This procedure was continued until all the steroid solution had been added and a permanent light yellow colour remained. The solution was stirred for a further 5 minutes and then poured into aqueous sodium thiosulphate. The organic layer was separated, washed with water, dried over potassium carbonate and evaporated to dryness. The residue was crystallised from acetone to give $3\beta$-acetoxy-$5\alpha,6\beta$-dichloropregnan-20-one (85%); m.p. 187°.

b. Fluorination $3\beta$-Acetoxy-$5\alpha,6\beta$-dichloropregnan-20-one (1.4g) was dissolved in fluorotrichloromethane (250 ml) and chloroform (200 ml) containing sodium trifluoracetate (ca. 2g) and sodium fluoride (ca. 2g). The resulting solution was cooled to $-\kappa°$ and vigourously stirred, whereupon fluorine from four 750 cc bottles (10% v/v fluorine in nitrogen) was bubbled through the solution over a period of 8 hours. The reaction solution was then poured into aqueous sodium thiosulphate and the organic layer was separated, washed with water, dried over potassium carbonate and evaporated to dryness to yield crude $3\beta$-acetoxy-$5\alpha,6\beta$-dichloro-$14\alpha$-fluoropregnan-20-one.

The crude product was dissolved in ethanol containing zinc and ammonium acetate and refluxed for 3 hours. The resulting mixture was filtered and the filtrate was evaporated to dryness in vacuo. Water and chloroform were added to the solid residue, whereafter the organic layer was separated, washed with water, dried and evaporated. A portion of the solid residue so obtained was purified by liquid chromatography, eluting with cyclohexane containing 17% v/v ethyl acetate and 0.1% v/v pyridine, to yield $3\beta$-acetoxy-$14\alpha$-fluoro-pregn-5(6-en-20-one (400 mg, 65%); m.p. 128° (after recrystallisation from methanol); PMR spectrum includes signals at $\delta$ 5.30 (1H, m, 6-H), 4.50 (1H, m, $3\alpha$-H), 2.10 (21-Me), 2.00 (3—0.CO.$CH_3$), 1.00 (19-Me) and 0.75 (18-Me); FMR $\phi^*$ 162 ppm (J "/2 = ca. 80 Hz). (Found: C, 73.59; H, 8.96; F, 4.89; $C_{23}H_{33}FO_3$ requires C, 73.37; H, 8.83; F, 5.04%).

ii. $3\beta$-Acetoxypregna-5(6), 14-dien-20-one

The remainder of the crude product from (i) (b) above was dissolved in ethylene glycol (30 ml) containing pulverised sodium hydroxide (0.5g), and the resulting solution was stirred overnight under nitrogen at 70–80°. The reaction solution was then poured into water, the resulting mixture was extracted with chloroform, and the chloroform layer was washed with water and evaporated. The oily residue was chromatographed on silica gel and eluted with hexane containing 30% v/v ethyl acetate to give the title compound which was recrystallised from methanol (220 mg, 45% overall); m.p. 205°-8°; PMR spectrum includes signals at $\delta$ 5.33 (1H, m, 6-H), 5.10 (1H, m, 15-H), 3.53 (1H, m, $3\alpha$-H), 2.13 (21-Me), 1.00 (19-Me) and 0.87 (18-Me).

EXAMPLE 14

Fluorination of $6\beta$-Acetoxy-$3\alpha,5\alpha$-cyclopregnan-20-one using Molecular Fluorine a. Preparation of starting material Pregnenolone p-toluenesulphonate (8g, prepared by reaction of pregnolone with p-toluenesulphonyl chloride in pyridine) and potassium acetate (10g) were refluxed in a 1:1 mixture of acetone and water (300 ml) for 36 hours. The reaction mixture was then poured into water (1 liter) and the resulting mixture was extracted with chloroform. The chloroform layer was then washed with water, dried and evaporated, and the residue was recrystallised from acetone to give 6β-hydroxy-3α,5α-cyclopregnan-20-one; m.p. 176°.

A solution of this product in pyridine (80ml) and acetic anhydride (70 ml) was heated to 80° for 1 hour and was then stirred overnight. The resulting solution was poured into water and the mixture so obtained was extracted with chloroform. The chloroform layer was washed with water, dried and evaporated to give 6β-acetoxy-3α,5α-cyclopregnan-20-one (ca. 30% from pregnenolone); PMR spectrum includes signals at δ4.47 (1H, t, J=3Hz, 6α-H), 2.1 (21-Me), 2.03 (6β-O.-CO.$\underline{CH}_3$), 1.0 (19-Me) and 0.7 (18-Me).

b. Fluorination

6β-Acetoxy-3α,5α-cyclopregnan-20-one (1.5g) was dissolved in fluorotrichloromethane (250 ml) and chloroform (200 ml) containing sodium trifluoracetate (ca. 2g) and sodium fluoride (ca. 2g). The resulting solution was cooled to −78° and vigourously stirred, whereupon fluorine from four bottles (each containing 12 mmoles at 0.5 Kg/cm² diluted to 3.5 Kg/cm² with nitrogen) was passed through. The reaction solution was then poured into aqueous sodium thiosulphate and the organic layer was separated, washed with water, dried over potassium carbonate and evaporated to dryness. The residue was purified by liquid chromatography, eluting with cyclohexane containing 17% v/v ethyl acetate and 0.1% v/v pyridine, to give 6β-acetoxy-14α-fluoro-3α,5α-cyclopregnan-20-one, which was recrystallised from methanol in 37% yield; m.p. 104°; PMR spectrum includes signals at δ 4.56 (t, J=3 Hz, 6α-H), 2.1 (21-Me), 2.03 (6β-O. CO.$\underline{CH}_3$), 1.0 (19-Me) and 0.82 (18-Me); FMR φ* + 162 ppm (J w/2 = 80–90 Hz). (Found: C, 73.12; H, 8.88; F, 5.48; $C_{23}H_{33}FO_2$ requires C, 73.37; H, 8.83; F, 5.04%).

EXAMPLE 15

Fluorination of
6β-Acetoxy-3α,5α-cycloandrostan-17-one using Molecular Fluorine

6β-Acetoxy-3α,5α-cycloandrostan-17-one 1.5g, prepared from 3β-hydroxyandrost-5-en-17-one using the method of Example 14a) was dissolved in fluorotrichloromethane (250 ml) and chloroform (200 ml) containing sodium trifluoroacetate (ca. 2g) and sodium fluoride (ca. 2g). The resulting solution was cooled to −78° and vigourously stirred, whereupon fluorine from four bottles (each containing 14 mmoles, ca. 10% v/v in nitrogen) was passed through. The reaction solution was then poured into aqueous sodium thiosulphate and the organic layer was separated, washed with water, dried over potassium carbonate and evaporated to dryness. The residue was purified by liquid chromatography, eluting with cyclohexane containing 25% ethyl acetate and 0.1% v/v pyridine, and three fractions were collected. The least polar component was unreacted starting material (400 mg). The next fraction was 6β-acetoxy-9α-fluoro-3α,5α-cycloandrostan-17-one (27% corrected for recovered starting material); m.p. 110° (after recrystallisation from methanol); PMR spectrum includes signals at δ 4.57 (t, J= 3 Hz, 6α-H), 2.06 (6β-O. CO.$\underline{CH}_3$), 1.12 (19-Me) and 0.93 (18-Me); FMR φ* + 179 ppm (broad signal, Jw/2 = 80 Hz). (Found: C, 72.34; H, 8.53; F, 6.02; $C_{21}H_{29}FO_3$ requires C, 72.38; H, 8.39; F, 5.45%). The most polar fraction was 6β-acetoxy-14α-fluoro-3α,5α-cycloandrostan-17-one (20% corrected for recovered starting material); m.p. 118° (after recrystallisation from methanol); PMR spectrum includes signals at δ 4.63 (t, J=3 Hz, 6α-H), 2.06 (6β-O. CO.$CH_3$), 1.07 (19-Me) and 1.06 (18-Me); FMR φ* + 163 ppm (broad signal, J w/2 = 80 Hz). (Found: C, 72.53; H, 8.61; F, 5.60; $C_{21}H_{29}FO_3$ requires C, 72.38; H, 8.39; F, 5.45%).

EXAMPLE 16

Fluorination of
3β,21-Diacetoxy-16β-methyl-17α-nitrooxy 5α-pregnan-20-one using Molecular Fluorine 3β,21-Diacetoxy-16β-methyl-17α-nitrooxy-5α-pregnan-20 -one (1.5g, prepared by treating the corresponding 17α-ol with fuming nitric acid in acetic acid/acetic anhydride) was dissolved in a mixture of chloroform (200 ml) and fluorotrichloromethane (250 ml) containing sodium fluoride (ca. 2g) and sodium trifluoroacetate (ca. 2g). The resulting solution was then cooled to −75° C, vigourously stirred, and treated with fluorine (four 750 cc bottles each containing 0.5 Kg/cm² fluorine diluted to 3.5 Kg/cm² with nitrogen). The resulting reaction mixture was poured into aqueous sodium thiosulphate, and the organic phase was separated, washed twice with water, treated with 2-3 drops of pyridine, and dried over magnesium sulphate. The organic solvents were then evaporated to yield crude 3β,21-diacetoxy-9α-fluoro-16β-methyl-17α-nitrooxy-5α-pregnan-20-one as a white solid. A sample recrystallised from methanol exhibited the spectral characteristics $v_{max}$ 1750 (wide band, three carbonyl absorptions) and 1650 cm⁻¹ (17α-nitrate); PMR spectrum includes signals at 4.66 (centre of ABq, J=16 Hz, 21-$\underline{CH}_2$OAc, together with 3α-H resonance), 2.17 (s, C-21 acetoxy), 2.00 (s, 3-acetoxy), 0.9 and 0.77 (C-18 and C-19 methyl); FMR φ* 179 (broad, J ~ 80 Hz).

We claim:

1. A process for the 9α-electrophilic fluorination of a saturated steroid compound containing a hydrogen atom bound to a tertiary carbon atom, wherein said steroid has a formula:

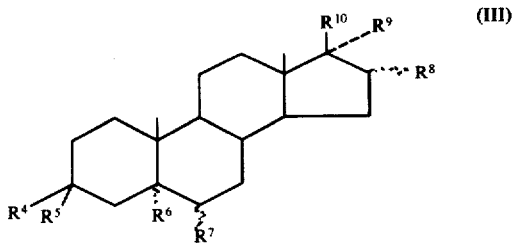

(III)

where $R^4$ represents protected hydroxy and $R^5$ represents hydrogen, or $R^4$ and $R^5$ together represent a keto or protected keto group, and $R^6$ and $R^7$ each represent hydrogen, or $R^4$ and $R^6$ together represent a 3,5-cyclo linkage, $R^5$ represents hydrogen and $R^7$ represents protected hydroxy; $R^8$ represents hydrogen, methyl or protected hydroxy; $R^9$ represents hydrogen, hydroxy or protected hydroxy and $R^{10}$ represents acetyl or substituted acetyl, or $R^9$ represents hydrogen and $R^{10}$ represents protected hydroxy, or $R^9$ and $R^{10}$ together represent a keto group; which comprises reacting the said steriod with an electrophilic fluorinating agent selected from the group consisting of molecular fluorine, pentafluorosulphur hypofluorite and lower fluoroalkyl hypofluorites in which the fluoroalkyl moiety contains at least two fluorine atoms per carbon atom, said fluorinating agent being substantially homogeneously dispersed in a liquid medium and said reaction being conducted in the presence of a free radical inhibitor to suppress formation of free fluorine radicals so that said hydrogen atom is electrophilically replaced by a fluorine atom, and recovering the thus-obtained fluoro steroid.

2. A process as claimed in claim 1 wherein the electrophilic fluorinating agent is selected from the group consisting of molecular fluorine diluted with nitrogen and trifluoromethyl hypofluorite.

3. A process as claimed in claim 1 wherein the free radical inhibitor is selected from the group consisting of oxygen, nitrobenzene, m-dinitrobenzene and benzoquinone.

4. A process as claimed in claim 1 wherein chloroform, methylene chloride or tetrahydrofuran is employed as a free radical inhibitor and the electrophilic fluorinating agent is molecular fluorine diluted with nitrogen.

5. A process as claimed in claim 1 wherein the fluorination is carried out in the presence of a substance which binds or adsorbs hydrogen fluoride.

6. A process as claimed in claim 1 wherein, after the fluorination, a base is added to the crude fluoro steroid product in order to stabilize the said product.

7. A process as claimed in claim 1 wherein $R^4$ represents acetoxy, trifluoroacetoxy or nitrooxy and $R^5$ represents hydrogen, or $R^4$ and $R^5$ together represent a keto group, and $R^6$ and $R^7$ each represent hydrogen, or $R^4$ and $R^6$ form a 3,5-cyclo linkage, $R^5$ represents hydrogen and $R^7$ represents acetoxy; $R^8$ represents hydrogen or methyl; $R^9$ represents hydrogen, hydroxy or nitrooxy and $R^{10}$ represents acetyl or acetoxyacetyl, or $R^9$ represents hydrogen and $R^{10}$ represents acetoxy or trifluoroacetoxy.

8. A process for the 14α-electrophilic fluorination of a saturated steroid compound containing a hydrogen atom bound to a tertiary carbon atom, wherein said steroid has a formula:

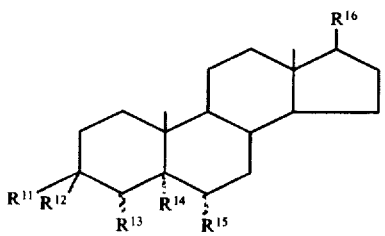

(V)

where $R^{11}$ represents protected hydroxy and $R^{12}$ represents hydrogen, or $R^{11}$ and $R^{12}$ together represent a keto or protected keto group, $R^{13}$ represents hydrogen and $R^{14}$ and $R^{15}$ each represent halogen, or $R^{14}$ together with $R^{13}$ or $R^{15}$ represents an epoxy group, the remaining $R^{13}$ or $R^{15}$ representing hydrogen, or $R^{11}$ and $R^{14}$ together represent a 3,5-cyclo linkage, $R^{12}$ and $R^{13}$ each represent hydrogen and $R^{15}$ represents protected hydroxy; and $R^{16}$ represents oxo, acetyl or protected hydroxy; which comprises reacting the said steroid with an electrophilic fluorinating agent selected from the group consisting of molecular fluorine, pentafluorosulphur hypofluorite and lower fluoroalkyl hypofluorites in which the fluoroalkyl moiety contains at least two fluorine atoms per carbon atom, said fluorinating agent being substantially homogeneously dispersed in a liquid medium and said reaction being conducted in the presence of a free radical inhibitor to suppress formation of free fluorine radicals so that said hydrogen atom is electrophilically replaced by a fluorine atom, and recovering the thus-obtained fluoro steroid.

9. A process as claimed in claim 8 wherein the electrophilic fluorinating agent is selected from the group consisting of molecular fluorine diluted with nitrogen and trifluoromethyl hypofluorite.

10. A process as claimed in claim 8 wherein the free radical inhibitor is selected from the group consisting of oxygen, nitrobenzene, m-dinitrobenzene and benzoquinone.

11. A process as claimed in claim 8 wherein chloroform, methylene chloride or tetrahydrofuran is employed as a free radical inhibitor and the electrophilic fluorinating agent is molecular fluorine diluted with nitrogen.

12. A process as claimed in claim 8 wherein the fluorination is carried out in the presence of a substance which binds or adsorbs hydrogen fluoride.

13. A process as claimed in claim 8 wherein, after the fluorination, a base is added to the crude fluoro steroid product in order to stabilize the said product.

14. A process as claimed in claim 8 wherein $R^{11}$ represents acetoxy, trifluoroacetoxy or nitrooxy and $R^{12}$ represents hydrogen, or $R^{11}$ and $R^{12}$ together represent a keto group, $R^{13}$ represents hydrogen and $R^{14}$ and $R^{15}$ each represent chloro or bromo, or $R^{11}$ and $R^{14}$ form a 3,5-cyclo linkage, $R^{12}$ and $R^{13}$ each represent hydrogen and $R^{15}$ represents acetoxy; and $R^{16}$ represents oxo, acetyl or acetoxy.

15. A process for the 17α-electrophilic fluorination of a saturated steroid compound containing a hydrogen atom bound to a tertiary carbon atom, wherein said steriod has a formula:

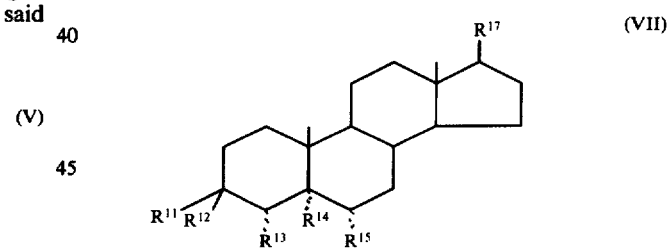

(VII)

wherein $R^{11}$ represents protected hydroxy and $R^{12}$ represents hydrogen, or $R^{11}$ and $R^{12}$ together represent a keto or protected keto group, $R^{13}$ represents hydrogen and $R^{14}$ and $R^{15}$ each represent halogen, or $R^{14}$ together with $R^{13}$ or $R^{15}$ represents an epoxy group, the remaining $R^{13}$ or $R^{15}$ representing hydrogen, or $R^{11}$ and $R^{14}$ together represent a 3,5-cyclo linkage, $R^{12}$ and $R^{13}$ each represent hydrogen and $R^{15}$ represents protected hydroxy; and $R^{17}$ represents a $C_{2-12}$ saturated hydrocarbyl group which comprises reacting the said steriod with an electrophilic fluorinating agent selected from the group consisting of molecular fluorine, pentafluorosulphur hypofluorite and lower fluoroalkyl hypofluorites in which the fluoroalkyl moiety contains at least two fluorine atoms per carbon atom, said fluorinating agent being substantially homogeneously dispersed in a liquid medium and said reaction being conducted in the presence of a free radical inhibitor to suppress formation of free fluorine radicals so that said hydrogen atom is electrophilically replaced by a fluorine atom, and recovering the thus-obtained fluoro steroid.

16. A process as claimed in claim 15 wherein the electrophilic fluorinating agent is selected from the group consisting of molecular fluorine diluted with nitrogen and trifluoromethyl hypofluorite.

17. A process as claimed in claim 15 wherein the free radical inhibitor is selected from the group consisting of oxygen, nitrobenzene, m-dinitrobenzene and benzoquinone.

18. A process as claimed in claim 15 wherein chloroform, methylene chloride or tetrahydrofuran is employed as a free radical inhibitor and the electrophilic fluorinating agent is molecular fluorine diluted with nitrogen.

19. A process as claimed in claim 15 wherein the fluorination is carried out in the presence of a substance which binds or adsorbs hydrogen fluoride.

20. A process as claimed in claim 15 wherein, after the fluorination, a base is added to the crude fluoro steroid product in order to stabilize the said product.

21. A process as claimed in claim 15 wherein $R^{11}$ represents nitrooxy or trifluoroacetoxy; $R^{12}$ and $R^{13}$ each represent hydrogen; $R^{14}$ and $R^{15}$ both represent chloro or bromo or together form an epoxy group; and $R^{17}$ represents the group —CH(CH$_3$)·(CH$_2$)$_3$·CH(CH$_3$)$_2$.

22. A compound having the formula:

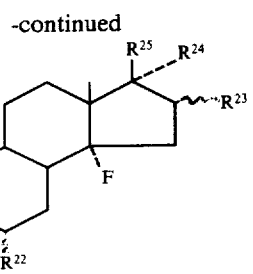

wherein $R^{18}$ represents hydroxy, nitroxy, acetoxy or trifluoroacetoxy and $R^{19}$ represents hydrogen or $R^{18}$ and $R^{19}$ together represent a keto group, $R^{20}$ represents hydrogen and $R^{21}$ and $R^{22}$ both represent hydrogen, chlorine or bromine or together form a carbon-carbon double bond or an epoxy group, and when $R^{18}$ and $R^{19}$ together represent a keto group $R^{20}$ and $R^{21}$ may together form a carbon-carbon double bond or an epoxy group, $R^{22}$ then being hydrogen, or $R^{18}$ and $R^{21}$ together form a 3,5-cyclo linkage, $R^{19}$ and $R^{20}$ then being hydrogen and $R^{22}$ being acetoxy; $R^{23}$ represents hydrogen or methyl; $R^{24}$ represents hydrogen or hydroxy and $R^{25}$ represents acetoxy, or $R^{24}$ and $R^{25}$ together represent a keto group.

23. The compound of claim 22 which is a 14α-fluoroandrost-4-ene-3,17-dione.

24. The compound of claim 22 which is a 14α-fluorotestosterone.

25. The compound of claim 22 which is 14α-fluoroprogesterone.

* * * * *